(12) United States Patent
Kim et al.

(10) Patent No.: US 9,643,959 B2
(45) Date of Patent: May 9, 2017

(54) TUBULIN POLYMERIZATION INHIBITOR AND METHOD FOR SYNTHESIZING SAME

(71) Applicant: KOREA RESEARCH INSTITUTE OF BIOSCIENCE AND BIOTECHNOLOGY, Daejeon (KR)

(72) Inventors: Bo Yeon Kim, Daejeon (KR); Thimmegowda N.R., Daejeon (KR); Sun Ok Kim, Daejeon (KR); Nak Kyun Soung, Daejeon (KR); Krisada Sakchaisri, Daejeon (KR); InJa Ryoo, Daejeon (KR); Chan-Mi Park, Daejeon (KR); Jong Seog Ahn, Daejeon (KR); Jae-Hyuk Jang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/787,243

(22) PCT Filed: Apr. 22, 2014

(86) PCT No.: PCT/KR2014/003484
§ 371 (c)(1),
(2) Date: Oct. 26, 2015

(87) PCT Pub. No.: WO2014/175623
PCT Pub. Date: Oct. 30, 2014

(65) Prior Publication Data
US 2016/0102078 A1     Apr. 14, 2016

(30) Foreign Application Priority Data

Apr. 26, 2013  (KR) .................. 10-2013-0046954
Apr. 21, 2014  (KR) .................. 10-2014-0047354

(51) Int. Cl.
*C07D 405/12*     (2006.01)

(52) U.S. Cl.
CPC .................. *C07D 405/12* (2013.01)

(58) Field of Classification Search
None
See application file for complete search history.

(56) References Cited

U.S. PATENT DOCUMENTS

| 7,060,714 | B2 | 6/2006 | Ahn et al. | 435/254.1 |
| 2003/0032603 | A1 | 2/2003 | Ahn et al. | 435/254.2 |
| 2005/0130221 | A1 | 6/2005 | Flynn et al. | 435/7.1 |
| 2010/0004208 | A1 | 1/2010 | Chaplin et al. | 514/100 |
| 2015/0182502 | A1 | 7/2015 | Kim et al. | 514/414 |

FOREIGN PATENT DOCUMENTS

WO   WO 2014/038894   * 3/2014 .......... A61K 31/404

OTHER PUBLICATIONS

National Center for Biotechnology Information. PubChem Substance Database; SID=1528787, https://pubchem.ncbi.nlm.nih.gov/substance/1528787 (accessed Oct. 17, 2016).*
Letter/Written Disclosure of the Information Disclosure Statement for the above-referenced application, mailed on Jan. 28, 2016, 2 pages.
Asami et al., "Protuboxepin A, a marine fungal metabolite, inducing metaphase arrest and chromosomal misalignment in tumor cells." Bioorg Med Chem. 20(12):3799-3806 (2012).
Goda et al., "Molecular mechanisms of the antitumor activity of SB225002: a novel microtubule inhibitor." Biochem Pharmacol. 85(12):1741-1752 (2013).
Hranjec et al., "Synthesis, antitumor evaluation and DNA binding studies of novel amidino-benzimidazolyl substituted derivatives of furyl-phenyl- and thienyl-phenyl-acrylates, naphthofurans and naphthothiophenes." Eur J Med Chem. 43(12):2877-2890 (2008).
Hu et al., "Phase-Transfer-Catalyzed Intramolecular Hydroaryloxylation and Hydroamination of C=C Triple Bonds: An Efficient Synthesis of Benzo[b]furan and 3-Methyleneisoindoline-1-one Derivatives." Green and Sustainable Chemistry 1(4):165-169 (2011).
Mukhanova et al., "New approach to synthesis of derivatives of 2-(5-hydroxybenzofuryl-3)naphthofurans," Chemistry of Heterocyclic Compounds 34(6):651-657 (1998).
Pubchem AC1OBLER (PubChem CID: 6876386), created Jul. 3, 2006, modified Nov. 21, 2015, available at http://pubchem.nchimlnunilugov/compound/6876386, accessed Nov. 23, 2015, 11 pages.
Srivastava et al., "Synthesis of 1-(3',4',5'-trimethoxy) phenyl naphtho[2,1b]furan as a novel anticancer agent."Bioorg Med Chem Lett. 16(4):911-914 (2006).
International Search Report and Written Opinion, issued Aug. 27, 2014, in connection with International Patent Application No. PCT/KR2014/003484, 9 pages. [English translation].
Official Action, issued Aug. 7, 2015, and translation, in connection with Korean Patent Application No. KR 10-2014-0047354, 6 pages. [Original document in Korean and English translation].

(Continued)

*Primary Examiner* — Alicia L Otton
(74) *Attorney, Agent, or Firm* — Dentons US LLP; Stephanie Seidman; Frank J. Miskiel

(57) ABSTRACT

The present invention relates to (E)-ethyl 2-(2-methyl-3-((2-(naphtho[2,1-b]furan-2-carbonyl)hydrazono)methyl)-1H-indol-1-yl)acetate as a novel tubulin polymerization inhibitor and a method for synthesizing the same. The compound of the present invention can inhibit mitosis and induce apoptosis and thus be used as an anticancer agent, by binding to tubulin to inhibit microtube polymerization. According to the synthesis method of the present invention, the reaction is simplified and the efficiency is 60% or higher, leading to a very high yield, thereby providing an effective synthesis method.

7 Claims, 14 Drawing Sheets

(56) References Cited

OTHER PUBLICATIONS

International Preliminary Report on Patentability, issued Oct. 27, 2015, in connection with International Patent Application No. PCT/KR2014/003484, 7 pages. [English translation].

* cited by examiner

TUBULIN POLYMERIZATION INHIBITOR AND METHOD FOR SYNTHESIZING SAME

TECHNICAL FIELD

The present invention relates to a novel tubulin polymerization inhibitor and a synthesis method thereof. More particularly, the present invention relates to (E)-ethyl 2-(2-methyl-3-((2-(naphtho[2,1-b]furan-2-carbonyl)hydrazono)methyl)-1H-indol-1-yl)acetate and a synthesis method thereof.

BACKGROUND ART

Microtubule is a major component of cytoskeleton, which is composed of tubulin heterodimer consisting of α-subunit and β-subunit. Microtubule is involved in a variety of cellular functions such as intracellular transportation, maintaining polarity, intracellular signal transduction, cell migration, and cell proliferation, etc. Microtubules form spindle fibers during mitosis, which allow chromosomes arranged in the center of a cell to separate and move to side ends of the cell. When the spindle fibers do not function well, cell division is suppressed, resulting in apoptosis. Thus, microtubules have attracted attention as a target for anticancer agents.

Microtubule-targeting drugs are broadly divided into two groups: microtubule stabilizes and microtubule destabilizes. First, microtubule stabilizers include taxane, pacilitaxel (Taxol), docetaxel, etc. which serve to prevent depolymerization of microtubules and enhance polymerization. Most microtubule stabilizers bind to the taxane-binding site or overlapping site on β-tubulin. Second, microtubule destabilizers include colchicine, vinca alkaloid, etc. which bind to the colchicine-binding site or vinca-binding site. Drugs that target the microtubules exert their effects at lower concentrations than those that affect microtubule polymers; however, both drugs suppress mitosis equally.

Most tubulin inhibitors exhibit drug resistance, which represents a major obstacle to improving the overall response and survival of cancer patients. Therefore, there has recently been a growing interest in the development of novel tubulin inhibitors that can overcome multidrug resistance, and thus a number of active compounds have been found. Moreover, in addition to the problem of resistance, the problem of neurotoxicity is one of the major side effects of tubulin inhibitors derived from complex natural products, which affects the quality of life of cancer patients. Further, low oral-bioavailability has been a limiting factor for convenient oral administration.

Therefore, there has recently been an increasing need for the development of novel tubulin inhibitors that have low neurotoxicity, no side effects, and excellent oral-bioavailability and are not affected by anticancer drug resistance mechanisms.

DISCLOSURE

Technical Problem

Therefore, the present inventors have screened the materials that can inhibit cell proliferation from the small-molecule library and found for the first time that "(E)-ethyl 2-(2-methyl-3-((2-(naphtho[2,1-b]furan-2-carbonyl)hydrazono)methyl)-1H-indol-1-yl)acetate" has an activity of inhibiting mitosis, thus completing the present invention.

An object of the present invention is to provide a novel tubulin polymerization inhibitor, (E)-ethyl 2-(2-methyl-3-((2-(naphtho[2,1-b]furan-2-carbonyl)hydrazono)methyl)-1H-indol-1-yl)acetate.

Another object of the present invention is to provide an effective synthetic route for the synthesis of a novel tubulin polymerization inhibitor, (E)-ethyl 2-(2-methyl-3-((2-(naphtho[2,1-b]furan-2-carbonyl)hydrazono)methyl)-1H-indol-1-yl)acetate.

However, the technical problems to be solved by the present invention are not limited to those mentioned above, and other problems that are not mentioned can be apparently understood by those skilled in the art from the following description.

Technical Solution

The present invention provides a compound, (E)-ethyl 2-(2-methyl-3-((2-(naphtho[2,1-b]furan-2-carbonyl)hydrazono)methyl)-1H-indol-1-yl)acetate, represented by the following Formula I:

[Formula I]

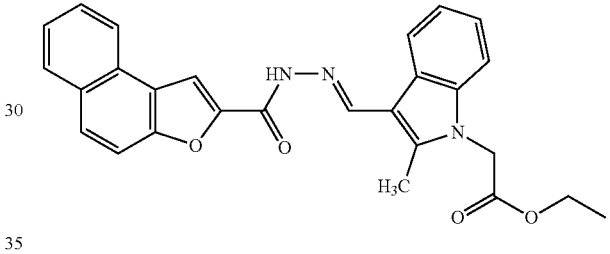

In a specific embodiment of the present invention, the compound is a tubulin polymerization inhibitor.

The present invention provides a method of synthesizing (E)-ethyl 2-(2-methyl-3-((2-(naphtho[2,1-b]furan-2-carbonyl)hydrazono)methyl)-1H-indol-1-yl)acetate, the method comprising: a first step of subjecting 2-hydroxy-1-naphthaldehyde and ethyl bromoacetate to condensation; a second step of subjecting naphtho[2,1-b]furan-2-carboxylic acid from the product obtained in the first step to esterification; a third step of subjecting the product obtained in the second step to hydrazinolysis; a fourth step of subjecting 2-methyl-1H-indole to formylation; a fifth step of subjecting the product obtained in the fourth step to nucleophilic substitution; and a sixth step of subjecting the product obtained in the third step and the product obtained in the fifth step to condensation.

In a specific embodiment of the present invention, the condensation in the first step uses anhydrous $K_2CO_3$ as a base dimethylformamide (DMF) as a solvent.

In another specific embodiment of the present invention, the esterification in the second step uses ethanol and $SOCl_2$.

In another specific embodiment of the present invention, the hydrazinolysis in the third step uses hydrazine hydrate.

In another specific embodiment of the present invention, the formylation in the fourth step is performed by reacting dimethylformamide (DMF) as a solvent with $POCl_3$, followed by further reacting 2-methyl-1H-indole thereto.

In another specific embodiment of the present invention, the nucleophilic substitution in the fifth step uses NaH as a base and ethyl bromoacetate.

In another specific embodiment of the present invention, the condensation in the sixth step uses acetic acid as a catalyst.

Advantageous Effects

The compound of the present invention binds to tubulin to inhibit microtubule polymerization, which can inhibit mitosis and induce apoptosis, and thus can be used as an excellent anticancer agent.

According to the synthesis method of the present invention, the reaction is simple, and the yield is very high with an efficiency of 60% or higher, thereby providing an effective synthesis method.

BEST MODE FOR CARRYING OUT THE INVENTION

Figure 1:
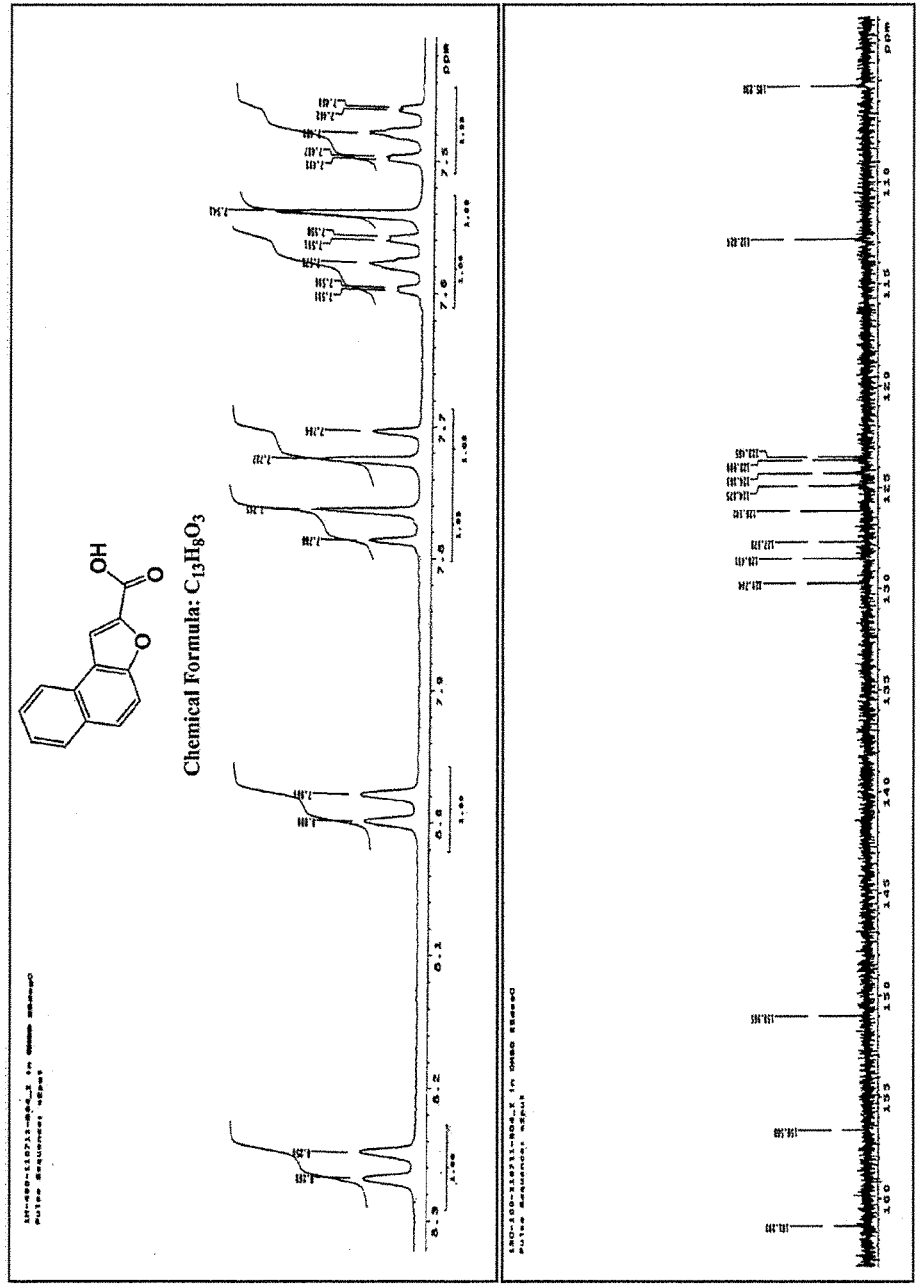
FIG. 1 shows the $^1$H NMR and $^{13}$C NMR spectra of compound (2a).

The chemical structure of the tubulin inhibitor compound of the present invention, "(E)-ethyl 2-(2-methyl-3-((2-(naphtho[2,1-b]furan-2-carbonyl)hydrazono)methyl)-1H-indol-1-yl)acetate", can be represented by the following Formula I.

This compound is in the form of bioactive heterocyclic scaffold naphthofuran derivative, to which N-substituted indole moiety is linked via an N-acylhydrazone structure.

[Formula I]

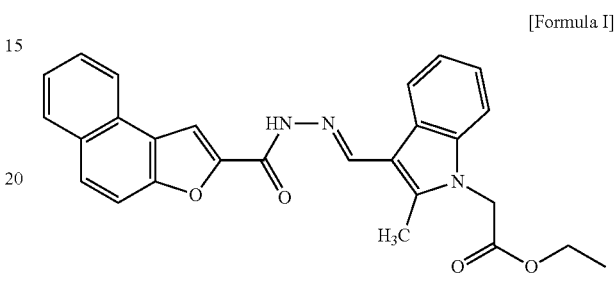

The tubulin inhibitor compound of the present invention binds to tubulin to inhibit microtubule polymerization, which can inhibit mitosis and induce apoptosis, and thus can be used as an excellent anticancer agent.

The synthesis method of the tubulin inhibitor compound of the present invention, "(E)-ethyl 2-(2-methyl-3-((2-(naphtho[2,1-b]furan-2-carbonyl)hydrazono)methyl)-1H-indol-1-yl)acetate", can be represented by the following Reaction Scheme:

Reaction Scheme 1. (E)-ethyl 2-(2-methyl-3-((2-(naphtho[2,1-b]furan-2-carbonyl)hydrazono)methyl)-1H-indol-1-yl)acetate

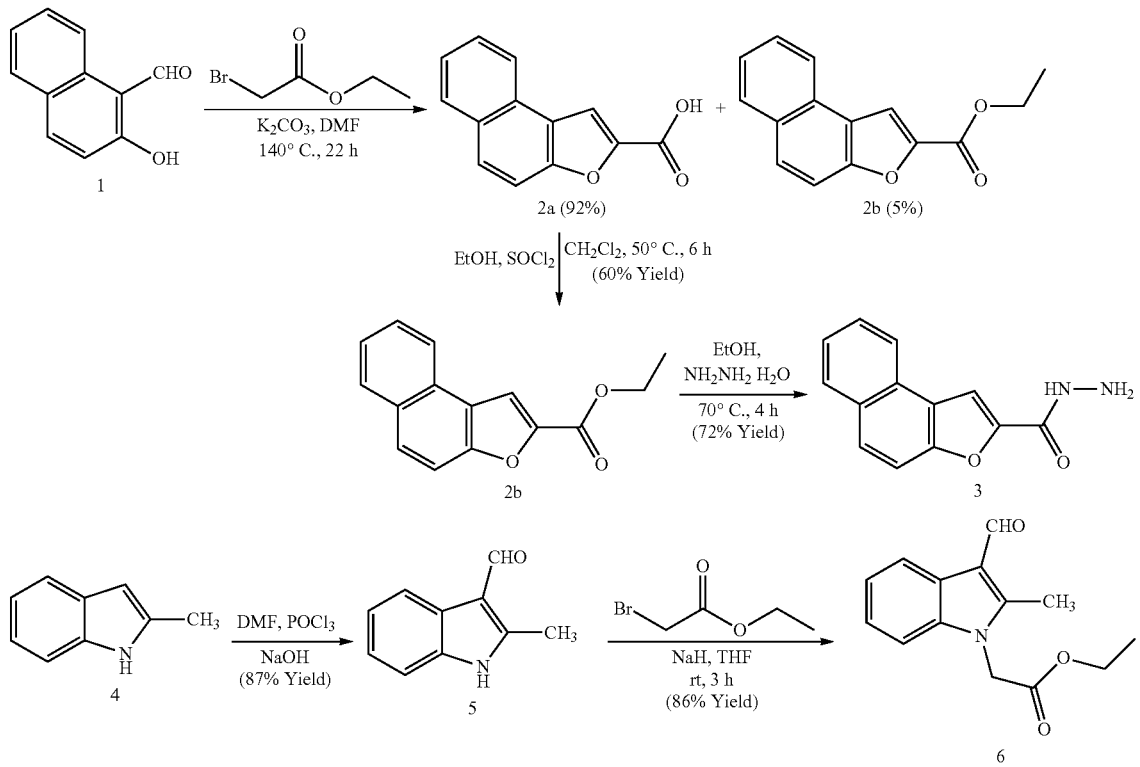

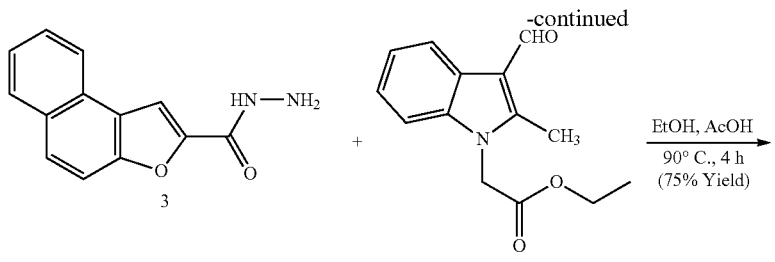
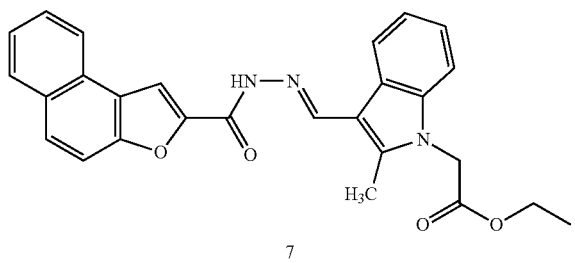

As can be seen from the above Reaction Scheme, the synthesis method of the present invention comprises six reaction steps such as condensation and cyclization, esterification, hydrazinolysis of esters, Vilsmeier-Haack formylation, nucleophilic substitution, and condensation of hydrazide and aldehyde.

The starting material in the first step of the synthetic pathway for the preparation of a final product compound (7) is 2-hydroxy-1-naphthaldehyde (1), with which ethyl bromoacetate or ethyl chloroacetate can be reacted to form naphtho[2,1-b]furan-2-carboxylic acid (2a). In this reaction, both condensation and cyclization occur in a single step with a yield of 90%.

As reaction conditions, anhydrous $K_2CO_3$, $Cs_2CO_3$ etc. can be used as a base, and dimethylformamide (DMF), N,N-dimethylacetamide (DMA), dimethylsulfoxide (DMSO), etc. can be used as a solvent. The reaction temperature of 2-hydroxy-1-naphthaldehyde (1), DMF, and anhydrous $K_2CO_3$ may preferably be 10 to 40° C., and the reaction time may preferably be 10 to 60 minutes. Moreover, the reaction temperature of the resulting mixture and ethyl bromoacetate may preferably be 100 to 200° C., and the reaction time may preferably be 10 to 30 hours.

The chemical structure of naphtho[2,1-b]furan-2-carboxylic acid (2a) can be determined by the $^1H$ NMR, $^{13}C$ NMR and ESIMS analyses. Seven aromatic proton signals were observed at δ 8.269-7.460 ppm in the $^1H$ NMR spectrum, and thirteen carbon signals were observed at δ 161.293-105.238 ppm in the $^{13}C$ NMR spectrum (see FIG. 1). Moreover, the molecular ion peak was observed at m/z 211.4[M–H]$^−$ in the mass spectrum, which corresponds to a molecular formula of $C_{13}H_8O_3$ (see FIG. 2).

In the second step of the reaction, naphtho[2,1-b]furan-2-carboxylic acid (2a) is converted into ester ethyl naphtho[2,1-b]furan-2-carboxylic acid (2b) by esterification with ethanol and $SOCl_2$, and the yield is 60%.

Here, dimethylformamide (DMF), ethanol, etc. can be used as a solvent, and the mixture may preferably be stirred at −10 to 10° C. for 10 to 60 minutes, followed by further stirring at 10 to 80° C. for 1 to 6 hours.

The chemical structure of ester ethyl naphtho[2,1-b]furan-2-carboxylic acid (2b) can be determined by the $^1H$ NMR and ESIMS analyses. Together with seven aromatic proton signals in the $^1H$ NMR spectrum, new peaks, quartet —$CH_2$ appeared at δ 4.424-4.370 ppm (J=7.2 Hz) and triplet —$CH_2$ appeared at δ 1.388-1.353 ppm (J=7.2 Hz) (see FIG. 3). Moreover, the molecular ion peaks were observed at m/z 241.4[M+H]$^+$ in the mass spectrum and at 263.4 [M+Na]$^+$ in the ESIMS spectrum, which corresponds to a molecular formula of $C_{15}H_{12}O_3$ (see FIG. 4).

In the third step of the reaction, ester ethyl naphtho[2,1-b]furan-2-carboxylic acid (2b) may be reacted with hydrazine hydrate to form naphtho[2,1-b]furan-2-carbohydrazide (3) as an intermediate compound with a yield of 72%.

Here, ethanol, methanol, etc. can be used as a solvent, and the mixture may preferably be heated at 50 to 90° C., stirred for 1 to 6 hours, and then cooled.

No peak was observed in the $^1H$ NMR spectrum of naphtho[2,1-b]furan-2-carbohydrazide (3), which corresponds to ester. The $^1H$ NMR spectrum showed a signal at δ 10.049 ppm for amide O=C—NH and a signal at δ 4.597 ppm for —$NH_2$ of hydrazide (which can be replaced with $D_2O$) (see FIG. 5). Moreover, the molecular ion peaks were observed at m/z 225.4 [M–H]$^−$, 227.4 [M+H]$^+$, and 249.4 [M+Na]$^+$ in the mass spectrum, which corresponds to a molecular formula of $C_{13}H_{10}N_2O_2$ (see FIG. 6).

In the fourth step of the reaction, the Vilsmeier-Haack formylation of 2-methyl-1H-indole (4) forms 2-methyl-1H-indole-3-carbaldehyde (5) with a yield of 87%. First of all, an electrophilic material can be formed by reacting a solvent with $POCl_3$ at low temperature. Then, 2-methyl-1H-indole-3-carbaldehyde (5) can be prepared by slowly adding 2-methyl-1H-indole (4) and sodium hydroxide or potassium hydroxide thereto.

Here, DMF, etc. can be used as a solvent, and the mixture may preferably be stirred at −10 to 10° C. for 10 to 60 minutes.

Figure 7:
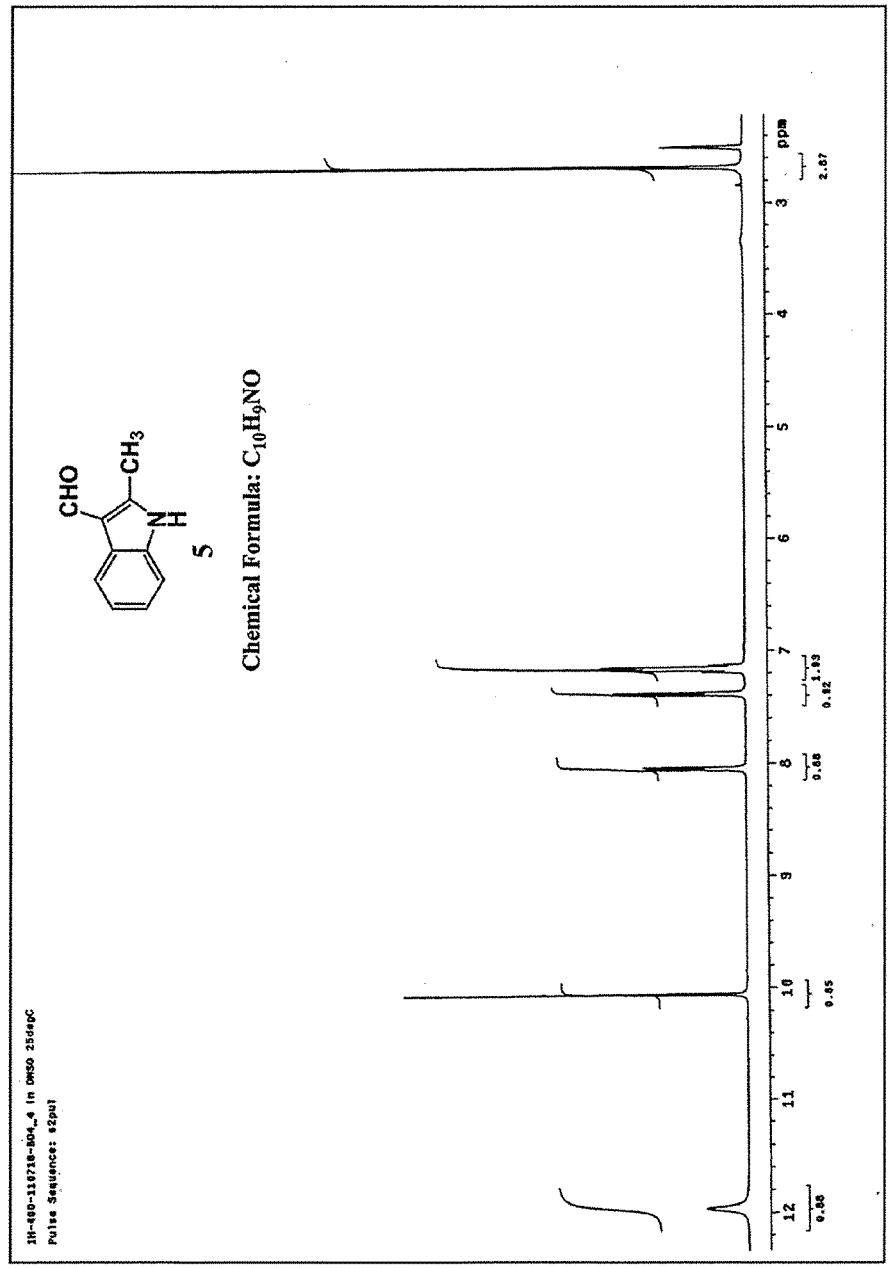
FIG. 7 shows the $^1$H NMR spectrum of compound (5).

The chemical structure of 2-methyl-1H-indole-3-carbaldehyde (5) can be determined by the $^1H$ NMR spectrum, and a new peak appeared at δ 10.058 ppm for —CHO instead of a single aromatic proton (see FIG. 7). The molecular ion peaks were observed at m/z 158.4 [M–H]$^−$, 160.4 [M+H]$^+$, and 182.3 [M+Na]$^+$ in the ESIMS spectrum, which corresponds to a molecular formula of $C_{10}H_9NO$ (see FIG. 8).

In the fifth step of the reaction, an intermediate ethyl 2-(3-formyl-2-1H-indol-1-yl)acetate (6), i.e. N-substitution compound of 2-methyl-1H-indole-3-carbaldehyde, may be formed by adding a base and ethyl bromoacetate or ethyl chloroacetate to 2-methyl-1H-indole-3-carbaldehyde (5). The yield is 86%.

Here, tetrahydrofuran (THF), DMF, acetone, etc. can be used as a solvent, and NaH, $K_2CO_3$ can be used as a base. The mixture may preferably be stirred at −10 to 10° C. for 10 to 60 minutes.

The chemical structure of ethyl 2-(3-formyl-2-1H-indol-1-yl)acetate (6) can be determined by the $^1$H NMR spectrum, and a new signal was observed at δ 11.962 ppm instead of an indole-NH signal. That is, quartet —$CH_2$ appeared at δ 4.208-4.155 ppm and triplet —$CH_3$ appeared at δ 1.241-1.205 ppm (see FIG. 9). The molecular ion peaks were observed at m/z 244.4 [M−H]$^-$, 246.4 [M+H]$^+$, and 268.4 [M+Na]$^+$ in the ESIMS spectrum, which corresponds to a molecular formula of $C_{14}H_{15}NO_3$ (see FIG. 10).

Lastly, in the sixth step of the reaction, "(E)-ethyl 2-(2-methyl-3-((2-(naphtho[2,1-b]furan-2-carbonyl)hydrazono)methyl)-1H-indol-1-yl)acetate", a final product (7), may be formed by condensing the hydrazide product (3) and the aldehyde product (6), which have been obtained in the previous steps, using a catalyst in a solvent. The yield is 75%.

Here, ethanol, methanol, etc. can be used as a solvent, and acetic acid, sulfuric acid, hydrochloric acid, etc. can be used as a catalyst. The mixture may preferably be stirred at 50 to 100° C. for 1 to 10 hours.

The chemical structure of the final product (7) can be determined by the $^1$H NMR, $^{13}$C NMR and mass analyses. The $^1$H NMR spectrum showed a single signal at δ 11.838 ppm for amide proton O═C—NH, a single signal at δ 8.862 ppm for azomethine proton —CH═N—, eleven aromatic proton signals at δ 8.438-7.198 ppm, a signal at δ 5.192 ppm for —N—$CH_2$, signals at δ 4.211-4.158 ppm for —O—$CH_2$, signals at δ 1.249-1.214 ppm for —$CH_3$, and a signal at δ 2.505 ppm for —$CH_3$ linked to an aromatic ring (see FIG. 11). The $^{13}$C NMR spectrum of the final product (7) showed a total of 27 carbon signals only (see FIG. 12), and the molecular ion peaks were observed at m/z 452.6 [M−H]$^-$, 454.6 [M+H]$^+$, and 476.5 [M+Na]$^+$ in the mass spectrum, which corresponds to a molecular formula of $C_{27}H_{23}N_3O_4$ (see FIGS. 13 and 14).

Next, preferred Examples will be provided for better understanding of the present invention. However, the following Examples are provided only for the purpose of illustrating the present invention, and the present invention is not limited by the Examples.

EXAMPLES

Unless otherwise stated in the experiments, all reactions were performed in oven-dried glassware under a nitrogen ($N_2$) atmosphere, and the mixture was stirred with a Teflon-coated magnetic bar. Moreover, the reaction was monitored using a fluorescent indicator (Merck) on a thin-layer chromatography (TLC) silica gel plate (Kieselgel 60 F254). The plate was visualized by ultraviolet light (UV) and treatment with acidic p-anisaldehyde stain or phosphomolybdic acid stain in 10% ethanol and $H_2SO_4$ followed by gentle heating. The solvent was removed by rotary evaporator under reduced pressure. The products of each reaction step were purified by flash column chromatography on silica gel (particle size: 40-63 μM, Merck) using a solvent system as described in the manual.

The Examples will be described in detail below.

Example 1

Synthesis of naphtho[2,1-b]furan-2-carboxylic acid (2a)

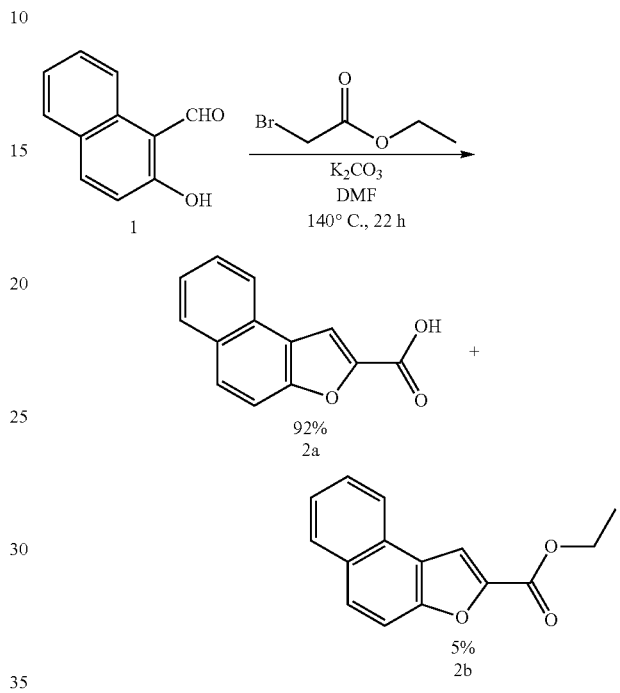

Under a nitrogen atmosphere, anhydrous potassium carbonate ($K_2CO_3$) (64.13 g, 290 mmol) was added to a solution of 2-hydroxy-1-naphthaldehyde (1) (10 g, 58 mmol) in anhydrous dimethylformamide (DMF) (150 mL). The mixture was stirred at room temperature for 30 minutes, to which ethyl bromoacetate (8.36 mL, 75 mmol) was added. Then, the resulting reaction mixture was heated at 140° C., stirred for 22 hours, and cooled at room temperature, and the reaction mixture was poured to ice cold water. The resulting solid was filtered, washed with water, and dried. Then, the product was recrystallized from diethyl ether to yield a purified product of naphtho[2,1-b]furan-2-carboxylic acid (2a) as a pale brown solid (11.3 g, yield 92%) ($R_f$=0.14) and ethyl naphtho[2,1-b]furan-2-carboxylic acid (2b) as a yellow solid (0.7 g, yield 5%) ($R_f$=0.87) (hexane:ethyl acetate=1:1).

Figure 2:
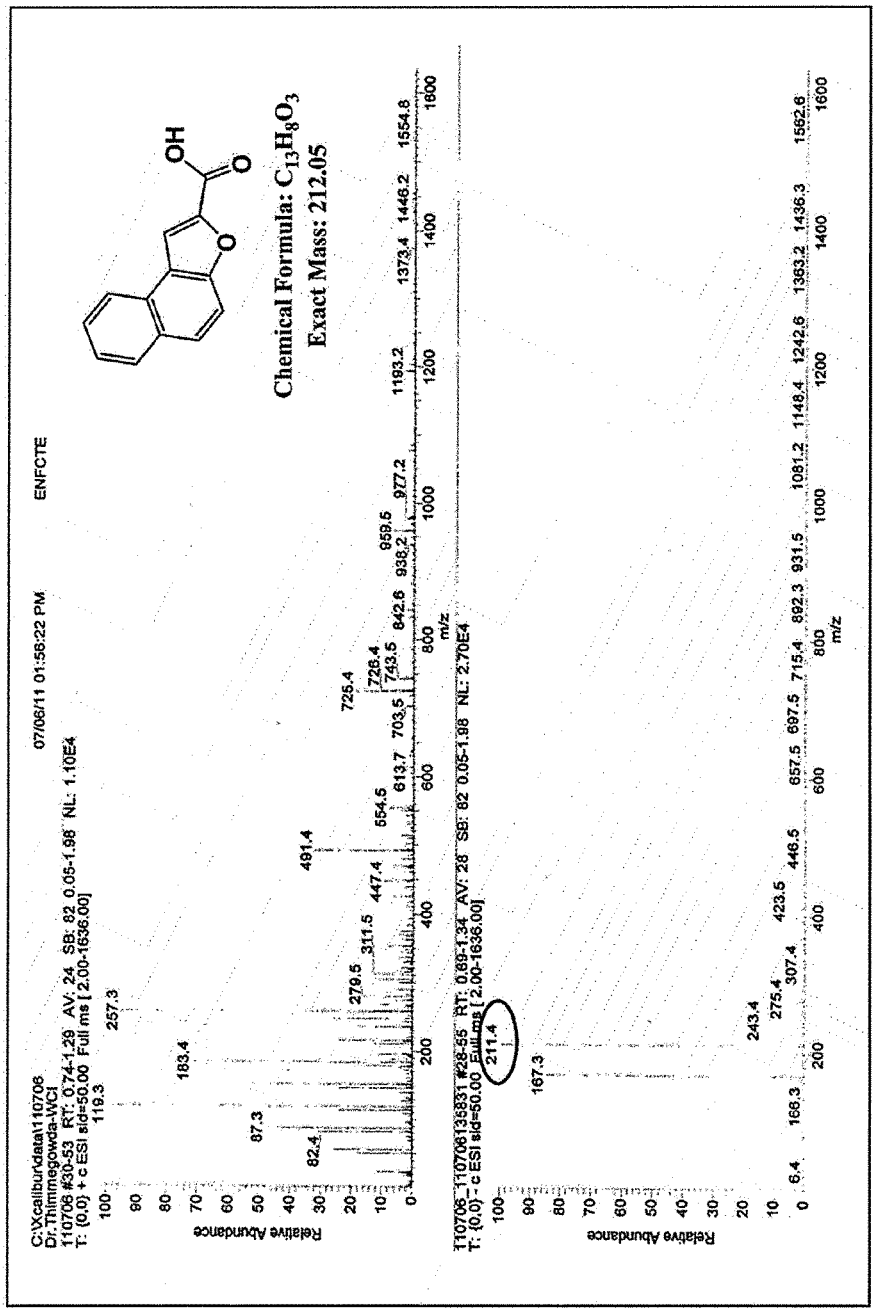
FIG. 2 shows the mass spectrum of compound (2a).

The $^1$H NMR and $^{13}$C NMR spectra of the resulting naphtho[2,1-b]furan-2-carboxylic acid (2a) is shown in FIG. 1, and the mass spectrum is shown in FIG. 2.

$^1$H NMR (400 MHz, DMSO-$d_6$) δ ppm: 8.269-8.250 (1H, d, J=7.6, Ar—H), 8.000-7.980 (1H, d, J=8, Ar—H), 7.788-7.765 (1H, d, J=9.2, Ar—H), 7.727-7.704 (1H, d, J=9.2, Ar—H), 7.558-7.599 (1H, t, J=7.6, Ar—H), 7.541 (1H, s, Ar—H), 7.498-7.460 (1H, t, J=7.6, Ar—H); $^{13}$C NMR (100 MHz, DMSO-$d_6$); δppm: 161.293, 156.558, 150.965, 129.704, 128.491, 127.679, 126.142, 124.875, 124.263, 123.6, 123.465, 112.824, 105.238; ESIMS found: m/z 211.4 [M−H]$^-$.

Example 2

Synthesis of ester ethyl naphtho[2,1-b]furan-2-carboxylic acid (2b)

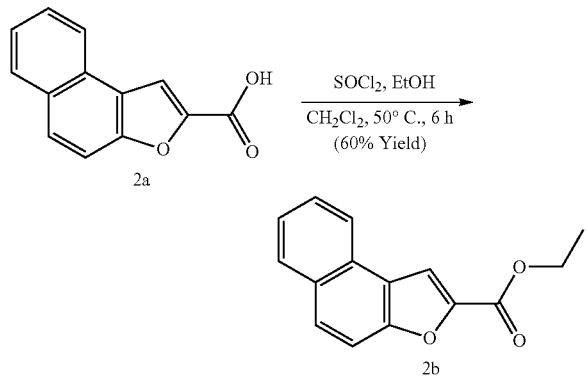

Naphtho[2,1-b]furan-2-carboxylic acid (2a) (10.0 g, 47 mmol) obtained in Example 1 was dissolved in dichloromethane ($CH_2Cl_2$) (100 mL) and anhydrous ethanol (EtOH) (150 mL) in an oven-dried round-bottom flask under a nitrogen atmosphere. The solution was cooled to 0° C. in an ice bath, to which thionyl chloride ($SOCl_2$) (5.1 mL, 70.5 mmol) was slowly added as droplet form via a syringe. The resulting reaction mixture was stirred at 0° C. for 30 minutes and 50° C. for 6 hours, the solvent was removed, and then the residue was diluted with $H_2O$ and ethyl acetate. After phase separation, the aqueous layer was extracted with ethyl acetate (3×250 mL), and the organic layer was dried over anhydrous $Na_2SO_4$, filtered, and concentrated under vacuum. The concentrate was recrystallized from diethyl ether and hexane to yield a purified product of ethyl naphtho[2,1-b]furan-2-carboxylic acid (2b) as a yellow solid (6.8 g, yield 60%).

Figure 3:
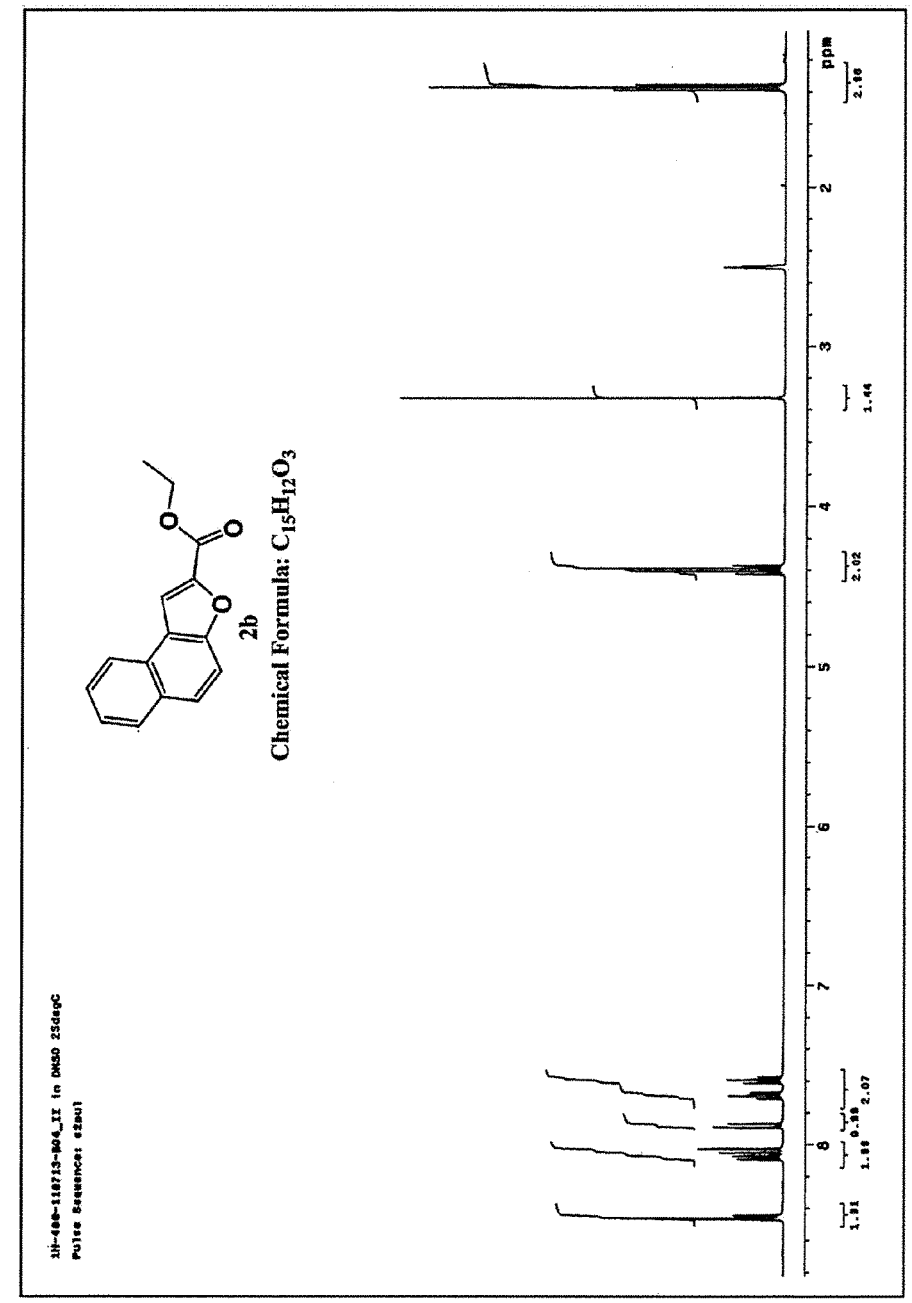
FIG. 3 shows the $^1$H NMR spectrum of compound (2b).
Figure 4:
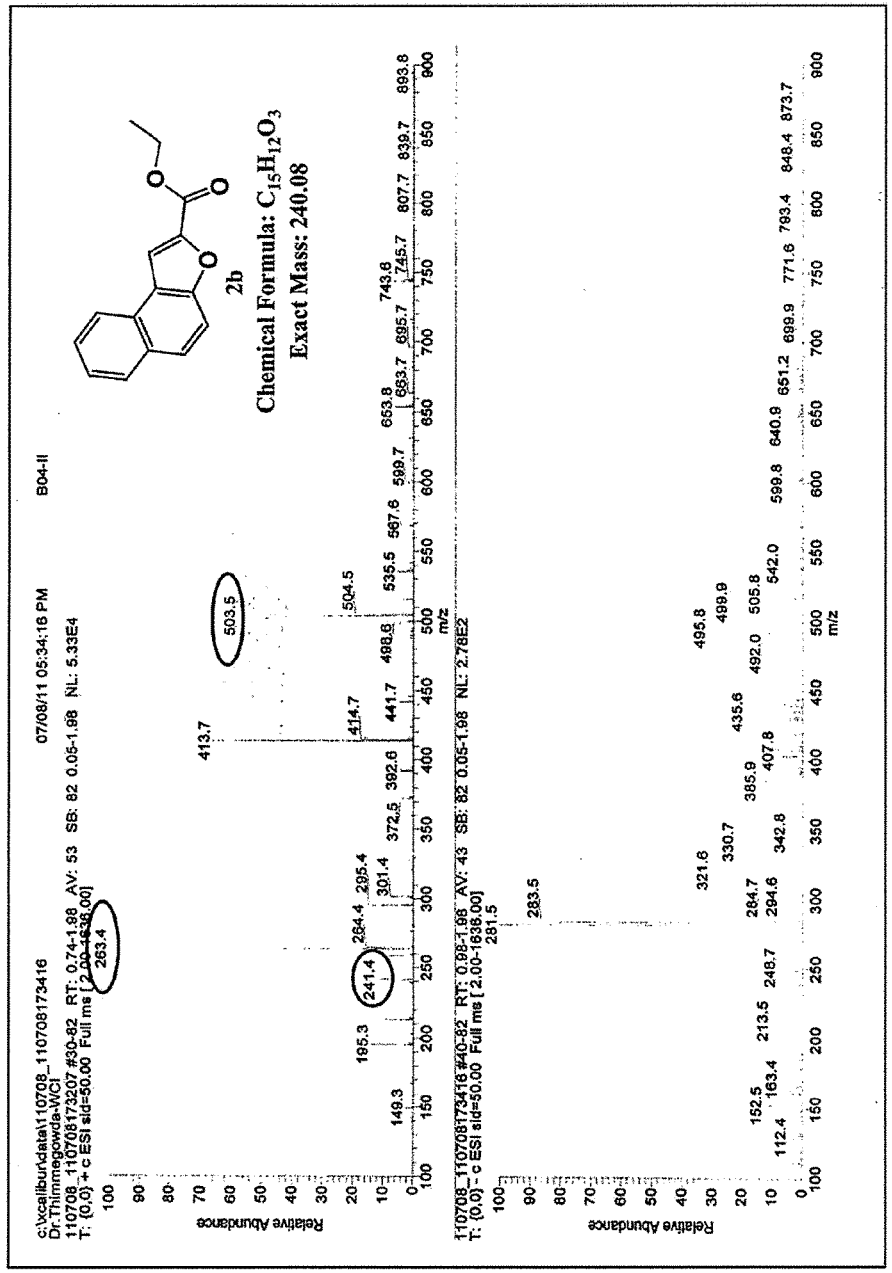
FIG. 4 shows the mass spectrum of compound (2b).

The $^1H$ NMR spectrum of the resulting ethyl naphtho[2,1-b]furan-2-carboxylic acid (2b) is shown in FIG. 3, and the mass spectrum is shown in FIG. 4.

$^1H$ NMR (400 MHz, DMSO-$d_6$) δ ppm: 8.466-8.448 (1H, d, J=7.2, Ar—H), 8.464 (1H, s, Ar—H), 8.091-8.071 (1H, d, J=8, Ar—H), 8.049-8.027 (1H, d, J=8.8, Ar—H), 7.892-7.868 (1H, d, J=8.8, Ar—H), 7.714-7.673 (1H, t, J=8.2, Ar—H), 7.614-7.573 (1H, t, J=8.2, Ar—H), 4.424-4.370 (2H, q, J=7.2, O—$CH_2$), 1.388-1.353 (3H, t, J=7.2, —$CH_3$); ESIMS found: m/z 241.4 [M+H]$^+$, 263.4 [M+Na]$^+$; $R_f$=0.87 (hexane:ethyl acetate=1:1).

Example 3

Synthesis of naphtho[2,1-b]furan-2-carbohydrazide (3)

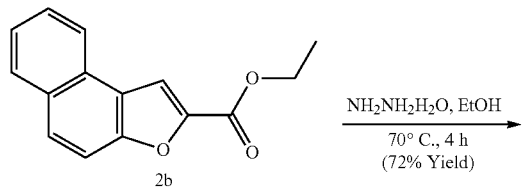

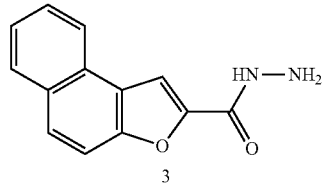

5 mL of hydrazine hydrate ($NH_2NH_2H_2O$) was added to an ethanol solution (EtOH) (100 mL) of ethyl naphtho[2,1-b]furan-2-carboxylic acid (2b) (5 g, 20.8 mmol) obtained in Example 2. The reaction mixture was heated at 70° C., stirred for 4 hours, and cooled at room temperature, and the reaction mixture was poured to ice cold water. The resulting solid was filtered, washed with water, and dried. Then, the product was recrystallized from diethyl ether and hexane to yield a purified product of naphtho[2,1-b]furan-2-carbohydrazide (3) as a pale yellow sold (3.4 g, yield 72%).

Figure 5:
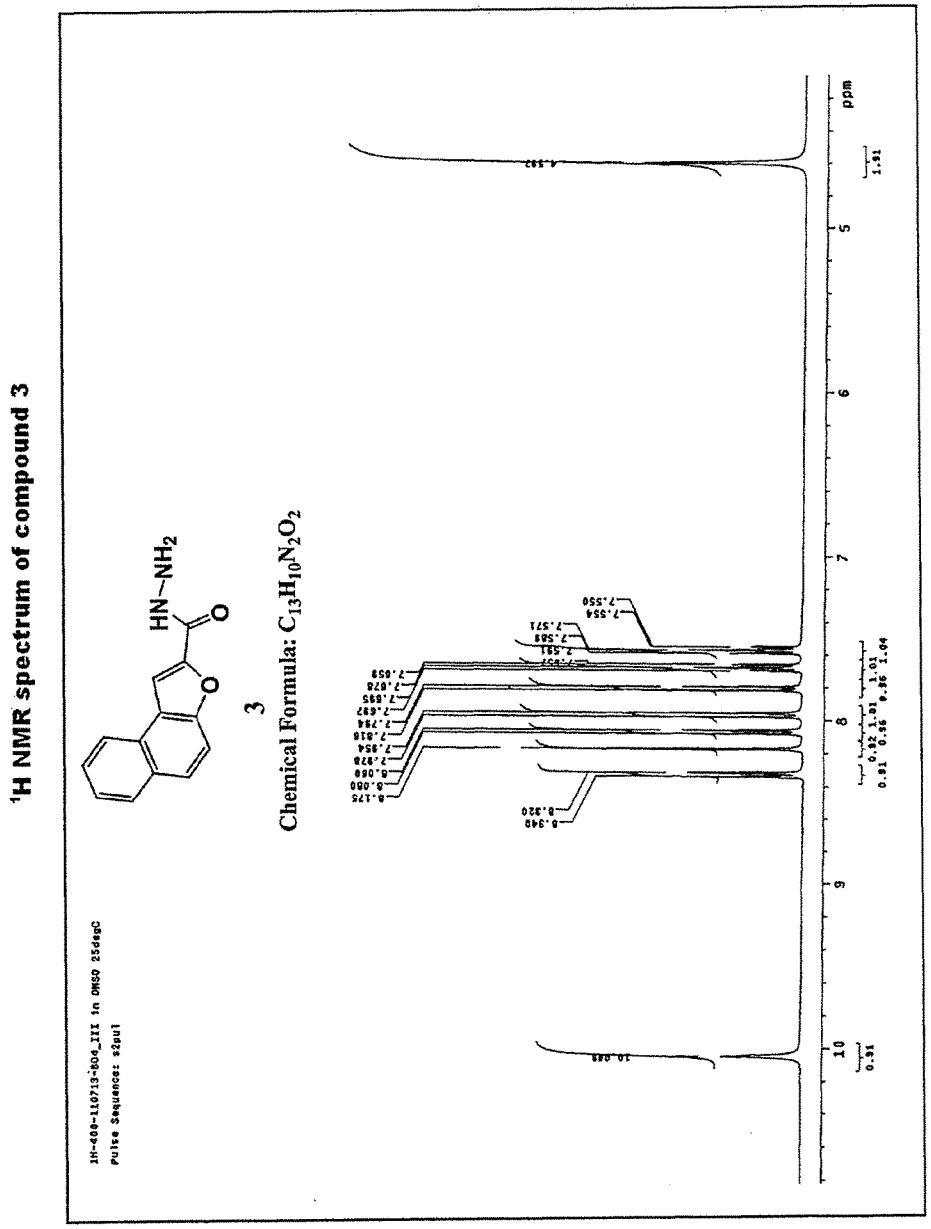
FIG. 5 shows the $^1$H NMR spectrum of compound (3).
Figure 6:
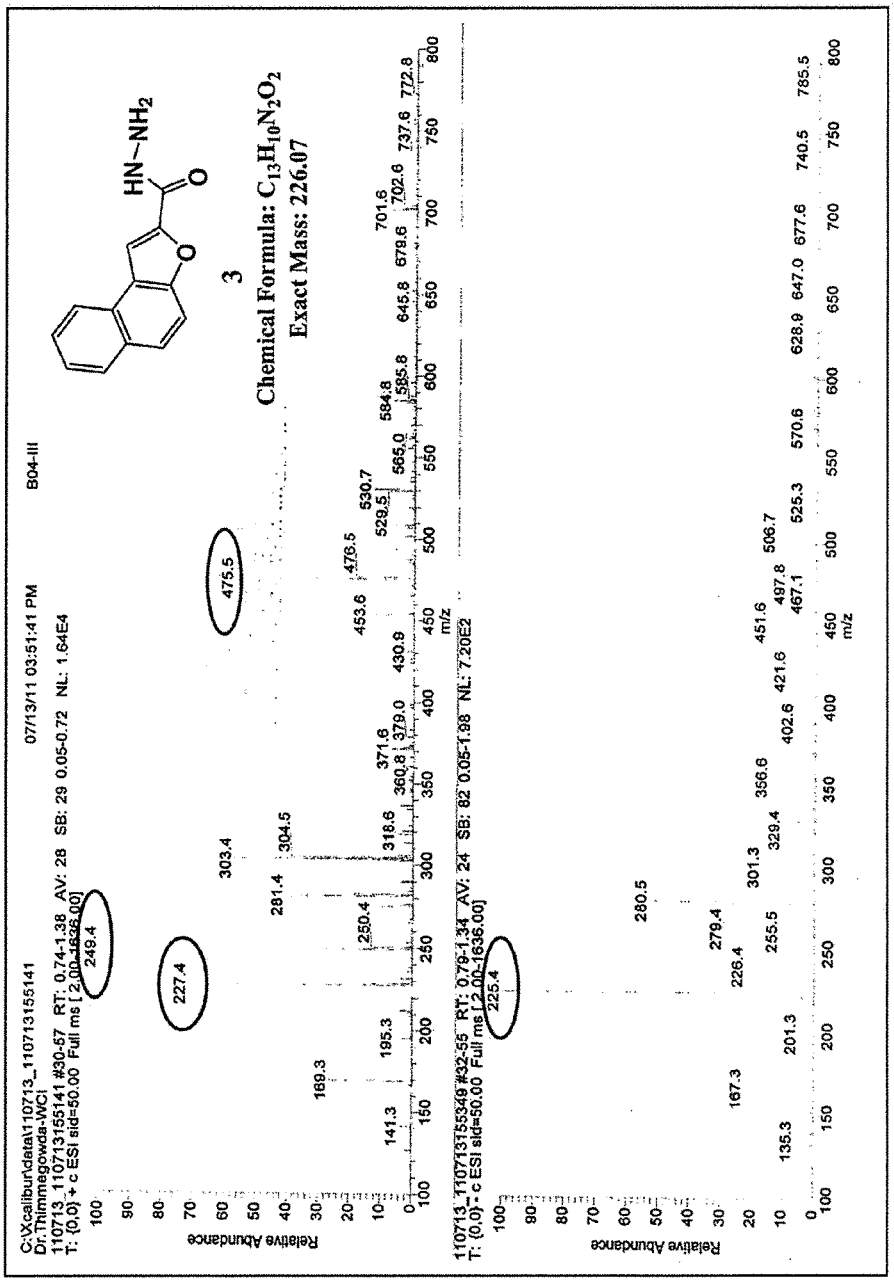
FIG. 6 shows the mass spectrum of compound (3).

The $^1H$ NMR spectrum of the resulting naphtho[2,1-b]furan-2-carbohydrazide (3) is shown in FIG. 5, and the mass spectrum is shown in FIG. 6.

$^1H$ NMR (400 MHz, DMSO-$d_6$) δ ppm: 10.049 (1H, s, O=C—NH—), 8.340-8.320 (1H, d, J=8.0, Ar—H), 8.175 (1H, s, Ar—H), 8.080-8.060 (1H, d, J=8.0, Ar—H), 7.978-7.954 (1H, d, J=9.6, Ar—H), 7.816-7.794 (1H, d, J=8.8, Ar—H), 7.697-7.657 (1H, t, J=8, Ar—H), 7.591-7.550 (1H, t, J=8.2, Ar—H), 4.597 (2H, s, —$NH_2$); ESIMS found: m/z 225.4 [M−H]$^−$, 227.4 [M+H]$^+$, 249.4 [M+Na]$^+$; $R_f$=0.17 (hexane:ethyl acetate=1:1).

Example 4

Synthesis of 2-methyl-1H-indole-3-carbaldehyde (5)

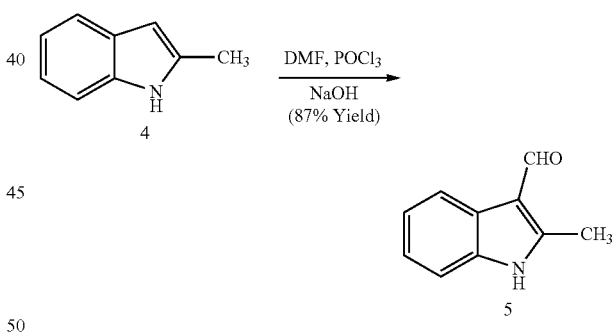

Anhydrous N,N-dimethylformamide (DMF) (12.6 mL, 163.4 mmol) was placed in an $N_2$-purged 250 ml 3-neck round bottom flask and cooled to 0° C. in an ice bath. Phosphorus oxychloride ($POCl_3$, 3.9 mL, 41.84 mmol) was slowly added thereto and stirred at 0° C. for 40 minutes. A solution of 2-methyl-1H-indole (4) (4.8 g, 36.5 mmol) in DMF (7.5 mL) was slowly added thereto while maintaining the temperature at 5° C. or lower. The resulting solution was stirred at 0° C. for 40 minutes, warmed at room temperature, and further stirred for 40 minutes. Then, a few pieces of ice were added to the flask, and a sodium hydroxide (NaOH) solution (16.5 g, 412.5 mmol dissolved in 50 mL of water) was added as droplet form through a dropping funnel while the mixture was vigorously stirred. The resulting solution was heated at 100° C., stirred for 30 minutes, and cooled at room temperature. The resulting pale yellow precipitate was filtered, washed with water, and dried. Then, the product was recrystallized from diethyl ether and hexane to yield a purified product of 2-methyl-1H-indole-3-carbaldehyde (5) as a pale yellow solid (5.0 g, yield 87%).

Figure 8:
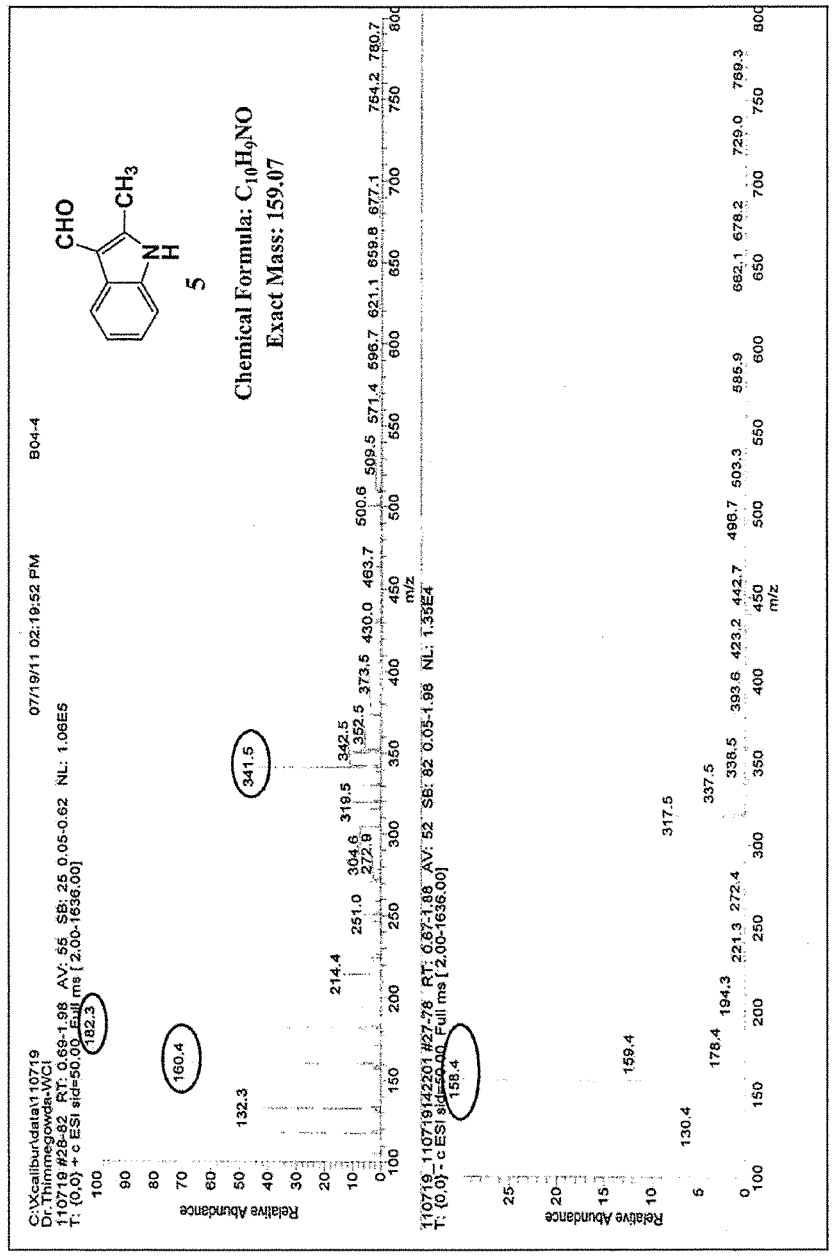
FIG. 8 shows the mass spectrum of compound (5).

The $^1$H NMR spectrum of the resulting 2-methyl-1H-indole-3-carbaldehyde (5) is shown in FIG. 7, and the mass spectrum is shown in FIG. 8.

$^1$H NMR (400 MHz, DMSO-d$_6$) δ ppm: 11.962 (1H, s, —NH), 10.058 (1H, s, —CHO), 8.054-80.33 (1H, dd, J=8.4, 2.0, Ar—H), 7.396-7.373 (1H, dd, J=6.6, 2.4, Ar—H), 7.188-7.130 (2H, m, Ar—H), 2.681 (3H, s, —CH$_3$); ESIMS found: m/z 158.4 [M−H]$^−$, 160.4 [M+H]$^+$, 182.3 [M+Na]$^+$; Rf=0.29 (hexane:ethyl acetate=1:1).

Example 5

Synthesis of ethyl 2-(3-formyl-2-1H-indol-1-yl)acetate (6)

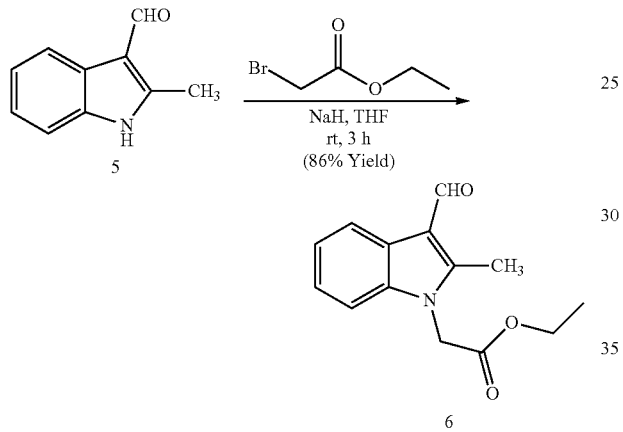

2-methyl-1H-indole-3-carbaldehyde (5) (3 g, 18.8 mmol) in tetrahydrofuran (THF) (50 mL) was cooled to 0° C. in an ice bath and mixed with sodium hydride (NaH) (60% dispersion in mineral oil) (1.5 g, 37.6 mmol). The mixture was stirred at 0° C. for 30 minutes, to which ethyl bromoacetate (2.5 mL, 28.6 mmol) was added. The resulting mixture was stirred at 0° C. for 30 minutes, warmed at room temperature, and further stirred for 3 hours. At this time, the TLC analysis showed the consumption of the starting material. The reaction mixture was cooled and further cooled down with ice water. The THF solvent was removed under vacuum, and the residue was diluted with H$_2$O and ethyl acetate. After phase separation, the aqueous layer was extracted with ethyl acetate (3×200 mL), and the combined organic layer was dried over anhydrous Na$_2$SO$_4$, filtered, and concentrated under vacuum. The concentrate was recrystallized from diethyl ether and hexane to yield a purified product of ethyl 2-(3-formyl-2-1H-indol-1-yl)acetate (6) as a pale yellow solid (4.0 g, yield 86%).

Figure 9:
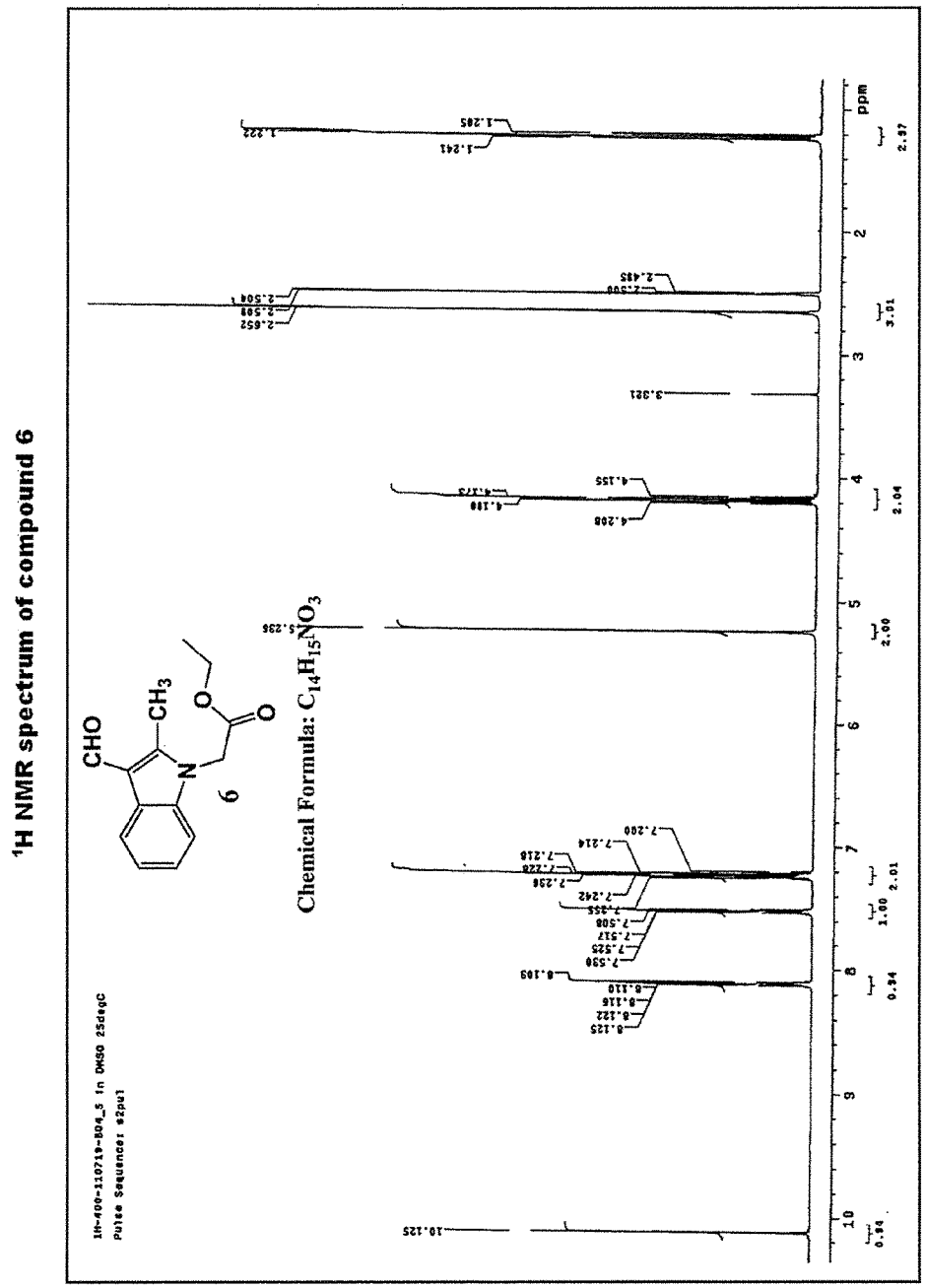
FIG. 9 shows the $^1$H NMR spectrum of compound (6).
Figure 10:
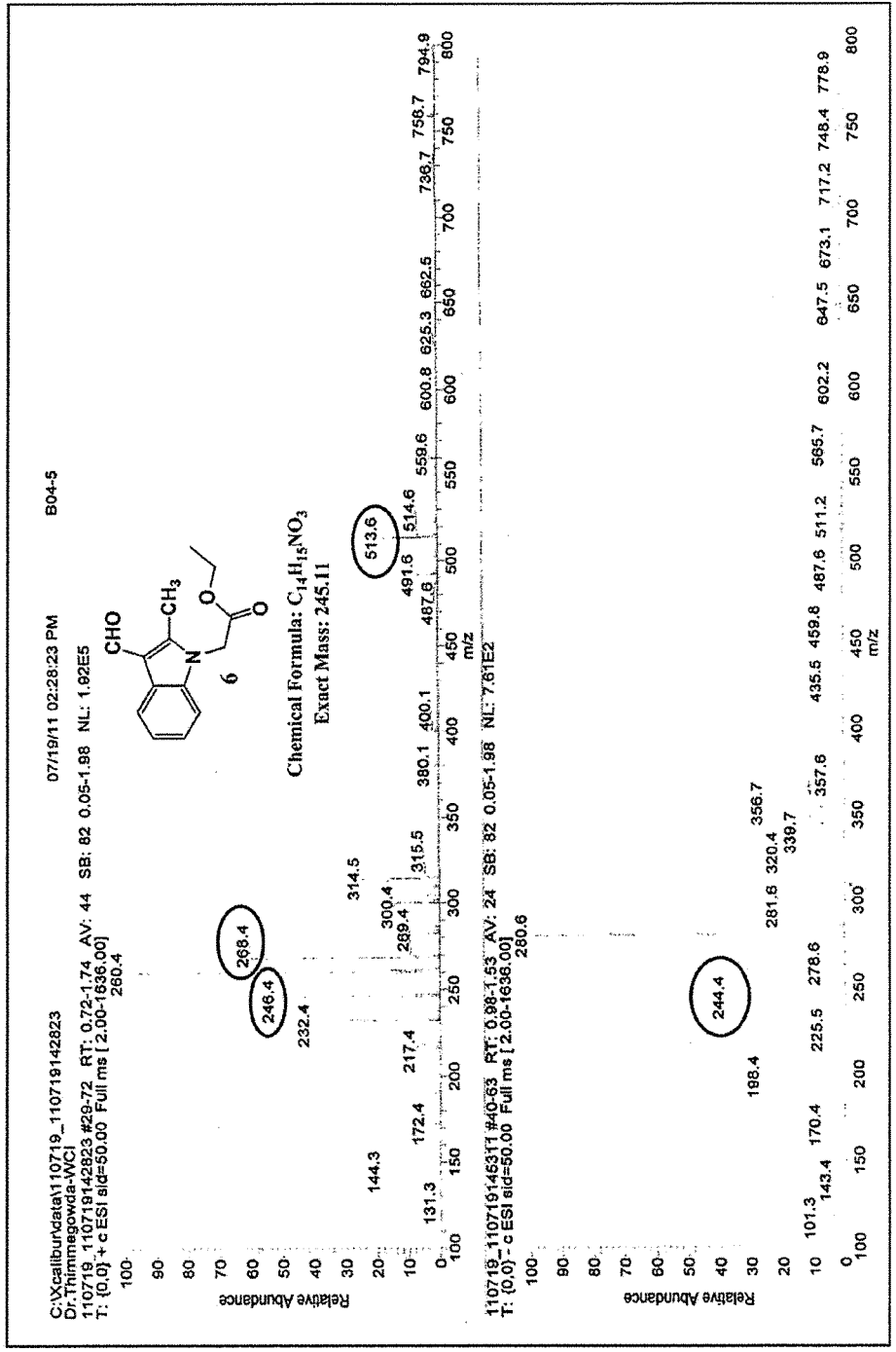
FIG. 10 shows the mass spectrum of compound (6).

The $^1$H NMR spectrum of the resulting ethyl 2-(3-formyl-2-1H-indol-1-yl)acetate (6) is shown in FIG. 9, and the mass spectrum is shown in FIG. 10.

$^1$H NMR (400 MHz, DMSO-d$_6$) δ ppm: 10.125 (1H, s, —CHO), 8.125-8.103 (1H, dd, J=7.6, 2.8, Ar—H), 7.530-7.508 (1H, dd, J=6.8, 2, Ar—H), 7.255-7.200 (2H, m, Ar—H), 5.236 (2H, s, —N—CH$_2$), 4.208-4.155 (2H, q, J=7.2, —O—CH$_2$), 2.652 (3H, s, —CH$_3$), 1.241-1.205 (3H, t, J=7.2, —CH$_3$); ESIMS found: m/z 244.4 [M−H]$^−$, 246.4 [M+H]$^+$, 268.4 [M+Na]$^+$, Rf=0.53 (hexane:ethyl acetate=2:1).

Example 6

Synthesis of (E)-ethyl 2-(2-methyl-3-((2-(naphtho[2,1-b]furan-2-carbonyl)hydrazono)methyl)-1H-indol-1-yl)acetate (7)

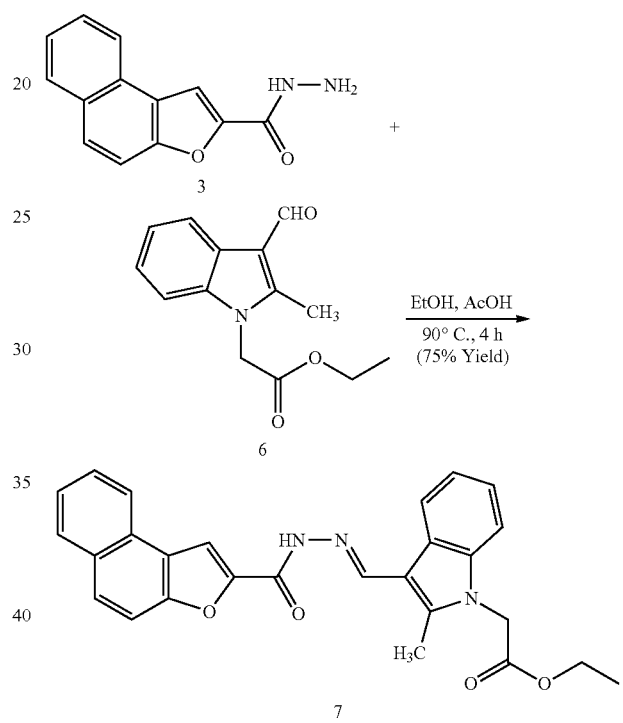

Naphtho[2,1-b]furan-2-carbohydrazide (3) solution (2 g, 8.8 mmol), ethyl 2-(3-formyl-2-1H-indol-1-yl)acetate (6) solution (2.16 g, 8.8 mmol) with a catalytic amount of acetic acid (AcOH) (10 ml) in ethanol (200 ml) was stirred at 90° C. for 4 hours. The TLC analysis showed the consumption of the starting material. The reaction mixture was cooled and ice water was added thereto. Then, the separated solid mass was filtered, washed with water, and dried. The residue was purified by silica gel flash column chromatography using hexane:ethyl acetate (1:1) as mobile phase to yield the final product, (E)-ethyl 2-(2-methyl-3-((2-(naphtho[2,1-b]furan-2-carbonyl)hydrazono)methyl)-1H-indol-1-yl)acetate (7), as a pale yellow solid (3 g, yield 75%).

Figure 11:
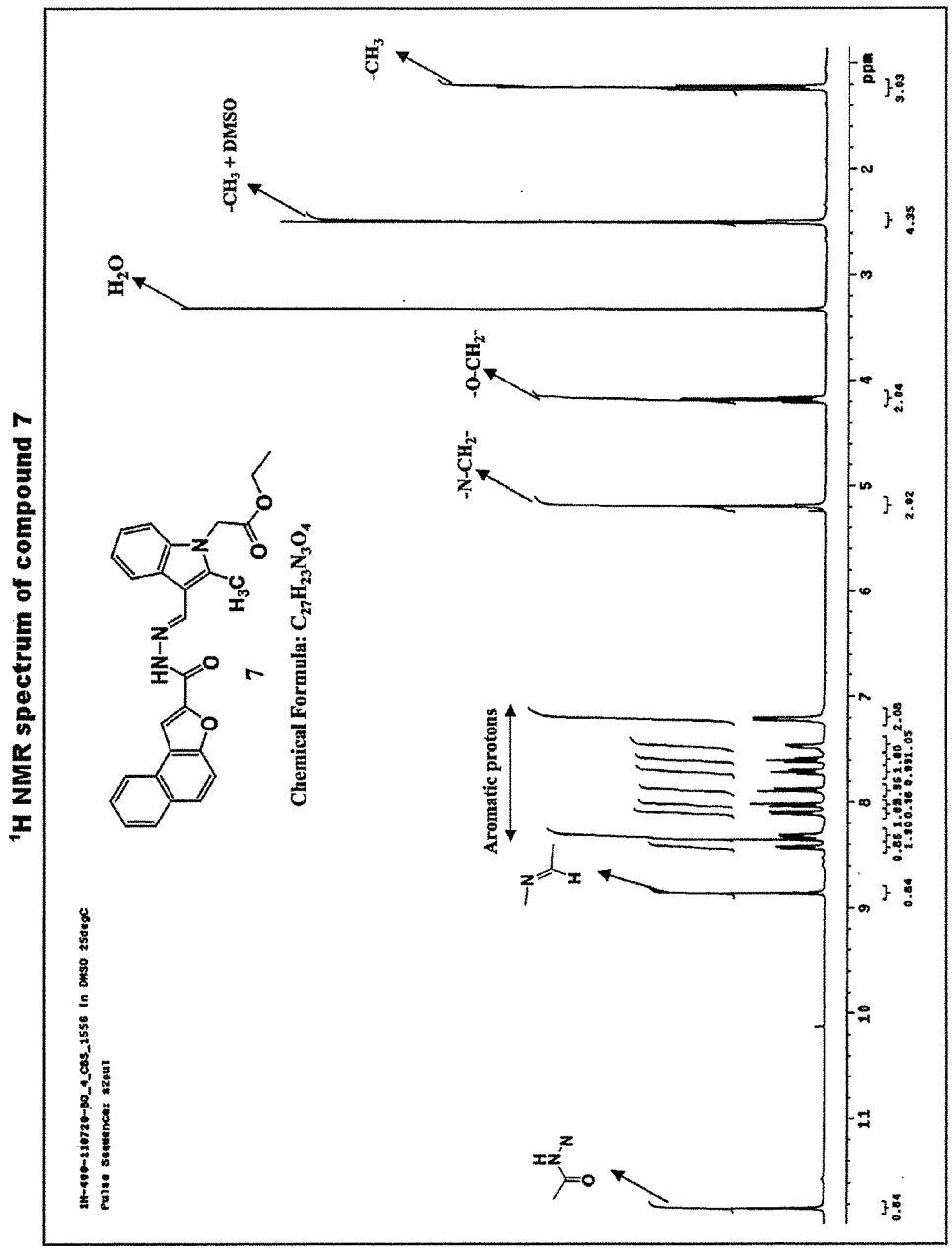
FIG. 11 shows the $^1$H NMR spectrum of compound (7).
Figure 12:
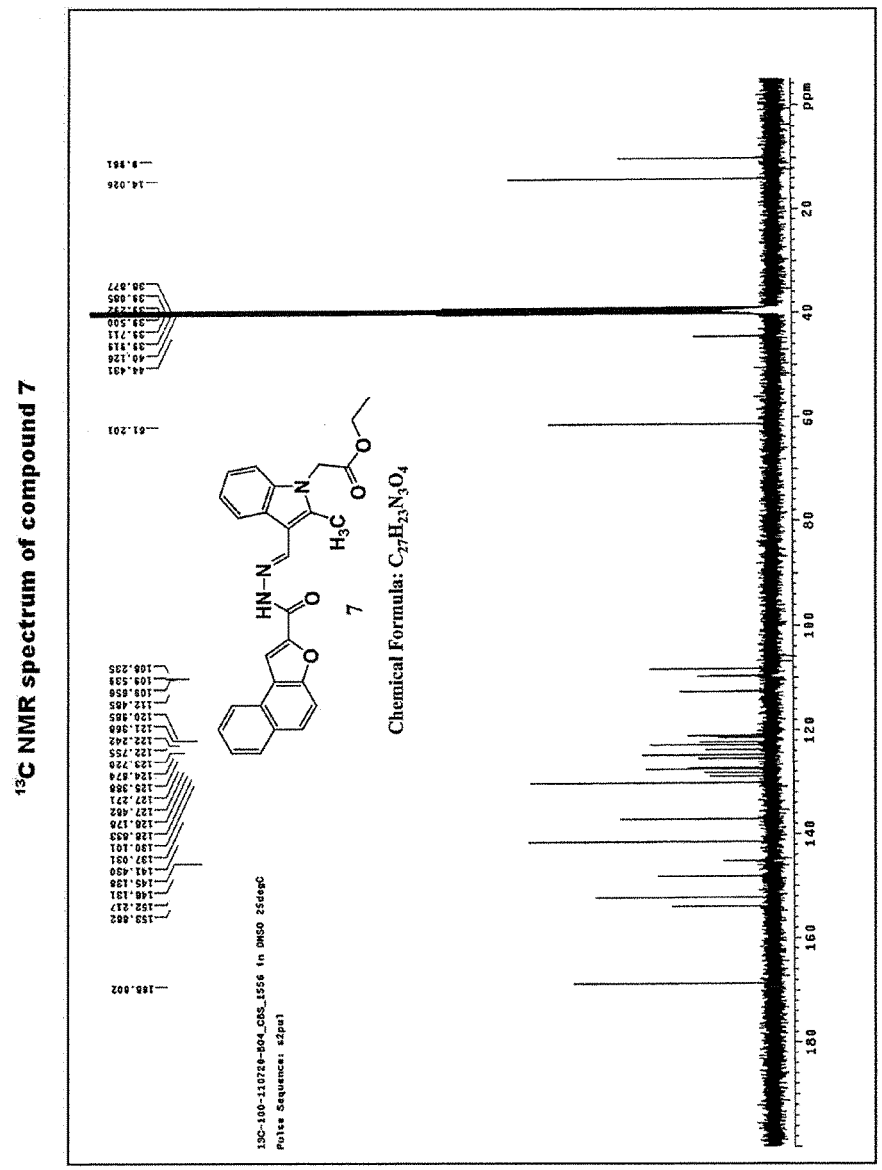
FIG. 12 shows the $^{13}$C NMR spectrum of compound (7).
Figure 13:
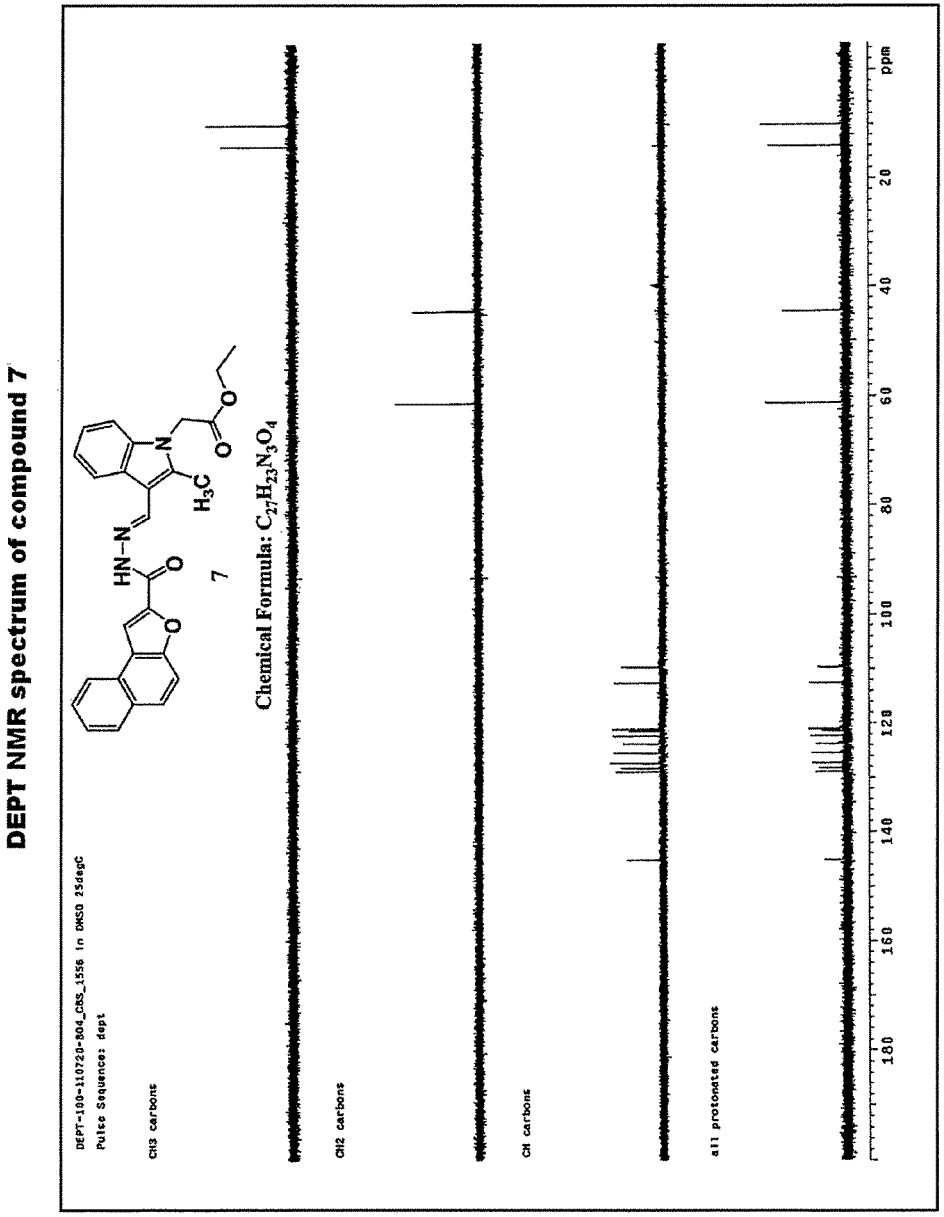
FIG. 13 shows the DEPT NMR spectrum of compound (7).
Figure 14:
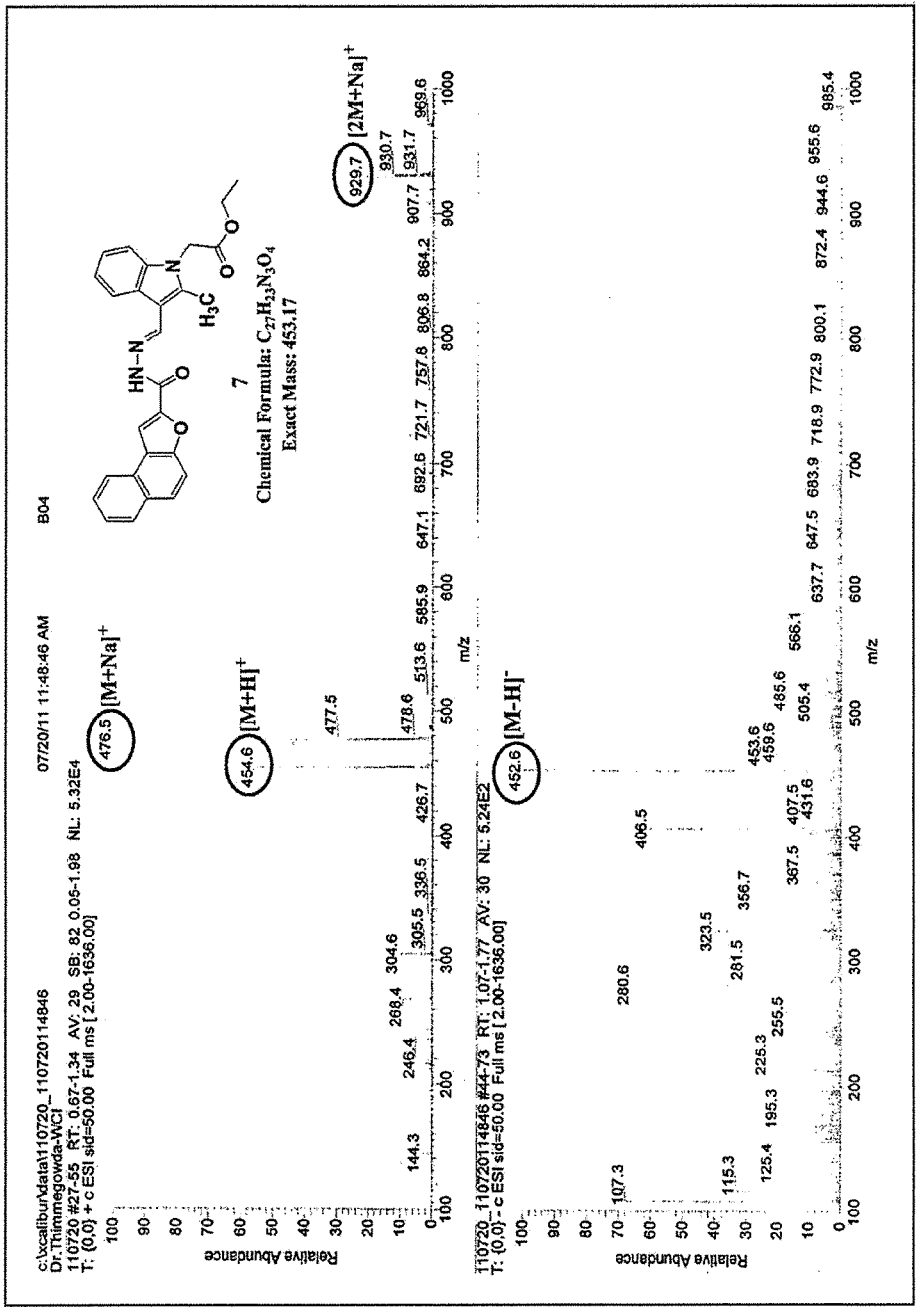
FIG. 14 shows the mass spectrum of compound (7).

The $^1$H NMR spectrum of the resulting (E)-ethyl 2-(2-methyl-3-((2-(naphtho[2,1-b]furan-2-carbonyl)hydrazono)methyl)-1H-indol-1-yl)acetate (7) is shown in FIG. 11, and the $^{13}$C NMR spectrum is shown in FIG. 12, the DEPT NMR spectrum of compound (7) is shown in FIG. 13, and the mass spectrum is shown in FIG. 14.

$^1$H NMR (400 MHz, DMSO-d$_6$) δ ppm: 11.838 (1H, s,

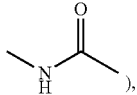

), 8.862 (1H, s,

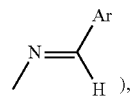

), 8.438-8.418 (1H, d, J=8, Ar—H), 8.355-8.307 (2H, dd, J=8.8, 3.6, Ar—H), 8.114-8.094 (1H, d, J=8.0, Ar—H), 8.041-8.018 (1H, d, J=8.0, Ar—H), 7.891-7.869 (1H, d, J=8.8, Ar—H), 7.731-7.694 (1H, t, J=7.2, Ar—H), 7.622-7.585 (1H, t, J=8.0, Ar—H), 7.483-7.461 (1H, t, J=8.8, Ar—H), 7.217-7.198 (2H, m, Ar—H), 5.192 (2H, s, —N—CH$_2$), 4.211-4.158 (2H, q, J=7.2, —O—CH$_2$), 2.505 (3H, s, —CH$_3$), 1.249-1.214 (3H, t, J=7.2, —CH$_3$); $^{13}$C NMR (100 MHz, DMSO-d$_6$): δppm: 168.602, 153.88, 152.217, 148.131, 145.138, 141.430, 137.031, 130.101, 128.833, 128.178, 127.482, 127.271, 125.388, 124.674, 123.720, 122.755, 122.242, 121.368, 120.985, 112.485, 109.656, 109.539, 108.235, 61.201, 44.431, 14.026, 9.961. ESIMS found: m/z 452.6 [M−H]$^-$, 454.6 [M+H]$^+$, 476.5 [M+Na]$^+$, R$_f$=0.50 (hexane:ethyl acetate=1:2).

INDUSTRIAL APPLICABILITY

As described above, the compound of the present invention binds to tubulin to inhibit microtubule polymerization, which can inhibit mitosis and induce apoptosis, and thus can be used as an excellent anticancer agent.

According to the synthesis method of the present invention, the reaction is simple, and the yield is very high with an efficiency of 60% or higher, thereby providing an effective synthesis method.

The invention claimed is:
1. A method for synthesizing (E)-ethyl 2-(2-methyl-3-((2-(naphtho[2,1-b]furan-2-carbonyl)hydrazono)methyl)-1H-indol-1-yl)acetate, which is represented by Formula I:

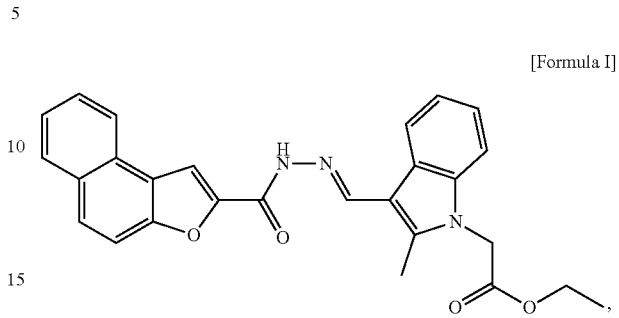

[Formula I]

the method comprising:
(a) a first step of subjecting 2-hydroxy-1-naphthaldehyde and ethyl bromoacetate to condensation;
(b) a second step of subjecting naphtho[2,1-b]furan-2-carboxylic acid from the product obtained in the first step to esterification;
(c) a third step of subjecting the product obtained in the second step to hydrazinolysis;
(d) a fourth step of subjecting 2-methyl-1H-indole to formylation;
(e) a fifth step of subjecting the product obtained in the fourth step to nucleophilic substitution; and
(f) a sixth step of subjecting the product obtained in the third step and the product obtained in the fifth step to condensation.

2. The method of claim 1, wherein the condensation in the first step uses anhydrous K$_2$CO$_3$ as a base and dimethylformamide (DMF) as a solvent.

3. The method of claim 1, wherein the esterification in the second step uses ethanol and SOCl$_2$.

4. The method of claim 1, wherein the hydrazinolysis in the third step uses hydrazine hydrate.

5. The method of claim 1, wherein the formylation in the fourth step is performed by reacting dimethylformamide (DMF) as a solvent with POCl$_3$, followed by further reacting 2-methyl-1H-indole thereto.

6. The method of claim 1, wherein the nucleophilic substitution in the fifth step uses NaH as a base and ethyl bromoacetate.

7. The method of claim 1, wherein the condensation in the sixth step uses acetic acid as a catalyst.

* * * * *